United States Patent [19]

Carlsson et al.

[11] Patent Number: 5,051,446

[45] Date of Patent: Sep. 24, 1991

[54] SUBSTITUTED 3-PHENOXY-1-ALKOXYCARBONYLALKYLAMINO-PROPANOL-2-S HAVING BETA RECEPTOR BLOCKING PROPERTIES

[75] Inventors: Enar I. Carlsson, Västra Frölunda; Bill B. Gustafsson, Bollebygd; Bo T. Lungren, Frillesas, all of Sweden

[73] Assignee: E. I. du Pont de Nemours & Co., Wilmington, Del.

[21] Appl. No.: 323,194

[22] Filed: Mar. 13, 1989

Related U.S. Application Data

[63] Continuation of Ser. No. 142,253, Jan. 5, 1988, abandoned, which is a continuation of Ser. No. 885,733, Jul. 21, 1986, abandoned, which is a continuation of Ser. No. 736,520, May 20, 1985, abandoned, which is a continuation of Ser. No. 460,837, Jan. 25, 1983, abandoned, which is a continuation of Ser. No. 262,474, May 11, 1981, abandoned.

[30] Foreign Application Priority Data

Jun. 2, 1980 [SE] Sweden ............................... 8004088

[51] Int. Cl.$^5$ .................. A61K 31/275; A61K 31/24; C07C 121/52; C07C 101/78
[52] U.S. Cl. ..................................... 514/522; 514/542; 558/417; 560/34
[58] Field of Search ........................ 560/34; 558/417; 514/542, 522

[56] References Cited

U.S. PATENT DOCUMENTS

| | | | |
|---|---|---|---|
| 3,793,365 | 2/1974 | Winter et al. | 560/39 |
| 3,998,790 | 12/1976 | Brändström et al. | 564/349 |
| 4,014,920 | 3/1977 | Jaeggi et al. | 560/39 |
| 4,244,969 | 1/1981 | Carlsson et al. | 560/39 |
| 4,387,103 | 6/1983 | Erhardt et al. | 560/42 |
| 4,450,173 | 5/1984 | Erhardt et al. | 424/309 |

FOREIGN PATENT DOCUMENTS

| | | |
|---|---|---|
| 2736106 | 2/1978 | Fed. Rep. of Germany . |
| 673413 | 6/1952 | United Kingdom . |
| 1260848 | 1/1972 | United Kingdom . |
| 1358803 | 7/1974 | United Kingdom . |
| 1492647 | 11/1977 | United Kingdom . |

OTHER PUBLICATIONS

Yusef, S., et al. "Early Intravenous Atenolol Treatment in Suspected Acute Myocardial Infarction", *The Lancet*, Aug. 9, 1980, pp. 273–276.

Frishman, W. H., "Clinical Pharmacology of the New Beta-Adrenergic Blocking Drugs. Part 12. Beta-Adrenocopetor Blockade in Myocardial Infarction: The Continuing Controversy", *American Heart Journal*, Apr. 1980, pp. 528–536.

Andersen, M., et al., "Effect of Alprenolol on Mortality Among Patients with Definite or Suspected Acute Myocardial Infarction", *the Lancet*, Oct. 27, 1979, pp. 865–867.

Sobel, B., "Propranolol and Threatened Myocardial," *The New England Journal of Medicine*, Jan. 25, 1979, pp. 191–193.

Mueller, H. S., "Beta Adrenergic Blockade in Acute Myocardial Infarction," *Hospital Formulary*, Nov., 1978, pp. 860–864.

Peter, T., "Reduction of Enzyme Levels by Propranolol After Myocardial Infarction," *Circulation*, Jun. 1978, pp. 1091–1095.

Lee, R. J., "Beta-Adrenergic Blockade in Acute Myocardial Infarction," *Life Sciences*, 1978, pp. 2539–2542.

*Primary Examiner*—Nicky Chan
*Attorney, Agent, or Firm*—Bernard, Rothwell & Brown

[57] ABSTRACT

The present invention relates to new compounds of the formula I

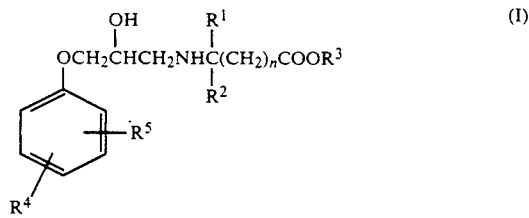

as well as their preparation, pharmaceutical preparations containing same, and method of treating acute myocardial infarction.

The compounds which possess beta-adrenoceptor blocking activity are very shortacting and are preferably intended for treatment of acute myocardial infarction by administration by means of injection.

5 Claims, No Drawings

SUBSTITUTED 3-PHENOXY-1-ALKOXYCARBONYLALKYLAMINO-PROPANOL-2-S HAVING BETA RECEPTOR BLOCKING PROPERTIES

This is a continuation of application Ser. No. 142,253 filed Jan. 5, 1988, now abandoned, which is a continuation of Ser. No. 885,733 filed July 21, 1986, now abandoned, which is a continuation of Ser. No. 736,520 filed May 20, 1985, now abandoned, which is a continuation of Ser. No. 460,837 filed Jan. 25, 1983, now abandoned, which is a continuation of Ser. No. 262,474 filed May 11, 1981, now abandoned.

DESCRIPTION

1. Technical Field

The present invention relates to new compounds having valuable properties in treating acute myocardial infarction and patients undergoing different kinds of surgery while exerting beta receptor blocking activity, process for their preparation, pharmaceutical preparations containing said compounds, and methods for treating acute myocardial infarction.

The object of the present invention is to obtain new compounds with beta adrenoceptor blocking activity and with such a short biological halflife that the degree of beta adrenoceptor blockade easily can be controlled by means of the parenteral administration rate. Such compounds can then be used in the vulnerable phase of acute myocardial infarction in order to reduce inferct size and also to prevent arrhythmias. The compounds may also be used as antiarrhythmics during various surgical procedures.

Generally, the new compounds can be used in the treatment of all indications where $\beta$-receptor blockers are used with the restriction that they can only be used by way of intravenous and topical administrations.

2. Background of the Invention

Compounds of the general structure

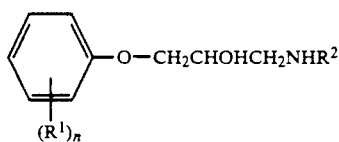

where n is an integer 1 to 3, and $R^1$ is i.a. any substituent of the group alkyl, alkenyl, alkynyl, alkoxy, alkenyloxy, alkynyloxy, halogen, nitro, cyano, alkoxyalkyl, alkoxyalkoxy, aminoalkylamino, optionally substituted with one or two alkyl groups, aminocarbonylaminoalkyl, optionally substituted with one or two alkyl groups, aryl, aralkyl, aralkoxy and aroyl, and $R^2$ is straight or branched alkyl, or hydroxyalkyl, cycloalkyl, or phenylalkyl, or phenoxyalkyl optionally substituted with alkyl, alkoxy, hydroxy, cyano, cyanomethyl, hydroxymethyl, or trifluormethyl, are known to possess betaadranoceptor blocking activity whereby they are used in treating angina pectoris, heart arrhythmias, hypertension, and glaucoma.

Further there are several indications that treatment with beta-adrenoceptor blockers in the early phase of acute myocardial infarction may reduce infarct size (of Waagstein et al, 1977 In: Acute and Long Term Medical Management of Myocardial Ischaemia. Eds: Å Hjalmarsson and L Wilhelmsen. Lindgren Soner AB, Molndal. pp. 346-357) and possibly also prevent arrhythmias.

However, since the first attempt to use beta-adrenoceptor blockers in acute myocardial infarction about 15 years ago, the treatment has been viewed with some doubt due to alarming reports of side effects (of Snow, P. J.: Effects of propranolol in myocardial infarction. Lancet 2: 551–553, 1965), and it is evident that treatment with beta-adrenoceptor blockers may be harmful to some patients with low cardiac output, severe heart failure and conduction disturbances. At present therefore very strict criteria are followed for the selection of patients for treatment with beta-adrenoceptor blockers during the acute phase of myocardial infarction. And even then some patients with myocardial infarction do not tolerate the beta-adrenoceptor blocker.

A great advantage in this connection would be to use a very shortacting beta-adrenoceptor blocker which could be given in a continuous intravenous infusion. The degree of beta-blockade could then be easily controlled by changes of the infusion rate. Furthermore, if beta-blockade is not tolerated by the patient the infusion could be stopped and the effect will then disappear within a few minutes due to the short halflife of the drug.

There would also be a great advantage to have a shortacting beta-adrenoceptor blocker available in anaesthesiology and in the intensive care units. For example, arrhythmias are common in connection with intubation and laryngoscopy. It is known that these arrhythmias can be treated with beta-adrenoceptor blockers. The now available betablockers however, are long acting and the blockade remains longer than needed.

The present para-substituted-3-phenoxy-1-alkoxycarbonyl-alkylamino-propanol-2-s of this patent application are all very shortacting, potent, $beta_1$-selective blockers which can be used in the indications mentioned above. These compounds should be infused intravenously at an infusion rate of 0.1–10 $\mu$mol/kg bodyweight x minute.

DISCLOSURE OF THE INVENTION

It has been found that the compounds of the general formula I

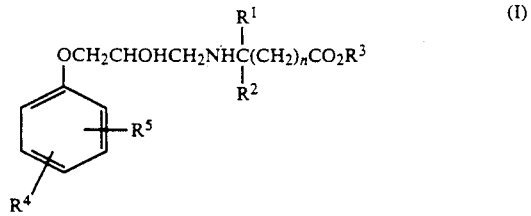

wherein $R^1$ and $R^2$ are each severally hydrogen, $R^3$ is alkyl having up to 7 carbon atoms, $R^4$ and $R^5$ are each severally selected from the group consisting of hydrogen, lower alkyl having up to 4 carbon atoms, lower alkenyl having up to 4 carbon atoms, lower alkoxy having up to 4 carbon atoms, cyano, $-(O)_n(CH_2)_m CONHR^6$, wherein $R^6$ is hydrogen or lower alkyl having up to 7 carbon atoms, n is an integer 0 or 1, and m is an integer 0, 1, 2, or 3, or $-(CH_2)_m NHCONHR^6$, wherein $R^6$, and m, have the meanings given above, and pharmaceutically acceptable acid addition salts thereof, and are shortacting, potent, beta₁-selective adrenoceptor blockers.

Alkyl $R^3$ is an alkyl having up tp 7 carbon atoms, preferably up to 5 carbon atoms, which alkyl group can be straight or branched. Thus, alkyl $R^3$ can be methyl, ethyl, n-propyl, isopropyl, n-butyl, isobutyl, or n-pentyl.

Alkyl $R^4$ and $R^5$ are a lower alkyl having up to 4 carbon atoms. Alkyl $R^4$ and $R^5$ are e.g. methyl, ethyl, propyl, isopropyl or tert. butyl.

Alkenyl $R^4$ and $R^5$ are a lower alkenyl having up to 4 carbon atoms. Alkenyl $R^4$ and $R^5$ are e.g. allyl.

Alkoxy $R^4$ and $R^5$ are a lower alkoxy having up to 4 carbon atoms. Alkoxy $R^4$ and $R^5$ are e.g. methoxy, ethoxy or isopropoxy.

Alkyl $R^6$ is equal to alkyl $R^3$.

Specific compounds of the invention are:
1. Ethyl N-[3-(2-cyanophenoxy)-2-hydroxypropyl]-3-aminopropanoate;
2. Ethyl N-[3-(2-N'-methylcarbamoylmethoxyphenoxy)-2-hydroxypropyl]-3-aminopropanoate;
3. Ethyl N-[3-(3-cyanophenoxy)-2-hydroxypropyl]-3-aminopropanoate;
4. Ethyl N-[3-[4-(2-N'-isopropylureido)ethylphenoxy]-2-hydroxypropyl]-3-aminopropanoate;
5. Ethyl N-[3-(3-methylphenoxy)-2-hydroxypropyl]-3-aminopropanoate
6. Ethyl N-[3-(2-allyl-4-carbamoylmethylphenoxy)-2-hydroxy-propyl]-3-aminopropanoate;
7. Ethyl N-[3-(2-cyano-4-methoxyphenoxy)-2-hydroxypropyl]-3-aminopropanoate;
8. Ethyl N-[3-(3-methoxyphenoxy)-2-hydroxypropyl]-3-aminopropanoate;
9. Ethyl N-[3-(2,3-dimethylphenoxy)-2-hydroxypropyl]-3-aminopropanoate
10. Propyl N-[3-(2-cyanophenoxy)-2-hydroxypropyl]-3-aminopropanoate;
11. Pentyl N-[3-(2-cyanophenoxy)-2-hydroxypropyl]-3-aminopropanoate These new compounds can be used at the treatment of acute myocardial infarctions and arrhythmias. One may also use them as intermediates at the preparation of other valuable pharmaceutical compounds. Salt forming acids may be used in preparing therapeutically acceptable salts of the compounds. These are: hydrohalogen acids, sulfuric acid, phosphoric acid, nitric acid, perchloric acid, aliphatic, alicyclic, aromatic or heterocyclic carboxy or sulfonic acids, such as formic, acetic, propionic, succinic, glycolic, lactic, malic, tartaric, citric, ascorbic, maleic, hydroxymaleic, or pyruvic acid, phenylacetic, benzoic, p-aminobenzoic, anthranilic, p-hydroxybenzoic, salicyclic or p-aminosalicyclic acid, embonic acid, methanesulfonic, ethanesulfonic, hydroxyethane sulfonic, ethylenesulfonic, halogenbenzensulfonic, toluenesulfonic, napthylsulfonic, or sulfanilic acid, methionine, tryptophane, lysine or arginine.

The substances are intended to be administered parenterally for acute and chronic treatment of above mentioned cardiovascular disorders.

The biological effects of the new compounds have been tested, and the different tests carried out will be shown and explained below.

The new compounds are obtained according to methods known per se. Thus, a compound of formula II

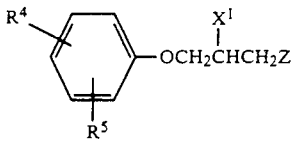

(II)

wherein $R^4$ and $R^5$ have the meanings given above, $X^1$ is a hydroxy group, Z is a reactive, esterified hydroxy group, or $X^1$ and Z together form an epoxy group, is reacted with an amine of the formula III

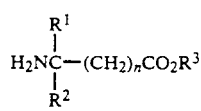

(III)

wherein $R^1$, $R^2$, $R^3$, and n have the meanings given above.

A reactive, esterified hydroxy group is particularly a hydroxy group esterified with a strong, inorganic or organic acid, preferably a hydrohalogen acid, as hydrochloric acid, hydrobromic acid, or hydroiodic acid, further sulfuric acid or a strong organic sulfonic acid, e.g. benzenesulfonic acid, 4-bromobenzenesulfonic acid, or 4-toluenesulfonic acid. Thus, Z is preferably chloro, bromo or iodo.

This reaction is carried out in a common way. At the use of a reactive ester as a starting material the preparation takes place preferably in the presence of a basic condensating agent and/or with an excess of an amine. Suitable basic condensating agents are e.g. alkali metal hydroxides as sodium or potassium hydroxide, alkali metal carbonates as potassium carbonate and alkali metal alcoholates as sodium methylate, potassium ethylate and potassium tert.-butylate.

The reaction is preferably carried out in an alkanol having 1 to 4 carbon atoms by refluxing the reactants in said solvent for a time long enough to give the compound of formula I, generally 1 to 12 hours. However, the reaction can be carried out in the presence of an excess of amine alone. The reaction can also take place in an autoclave.

Further, a compound of formula IV

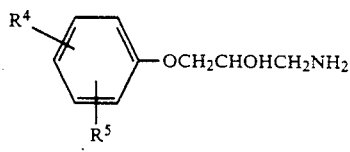

(IV)

wherein $R^4$ and $R^5$ have the meanings given above, is reacted with a compound of the formula V

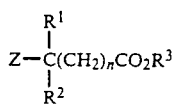

(V)

wherein Z and $R^1$, $R^2$, $R^3$, and n have the same meanings as given above.

This reaction is carried out in a common way, preferably in the presence of a basic condensating agent and/or an excess of an amine. Suitable basic condensating agents are e.g. alkaline alcoholates, preferably sodium or potassium alcoholate, or also alkaline carbonates as sodium or potassium carbonate.

This reaction is carried out usually with the presence of an alkanol having 1 to 3 carbon atoms being heated to reflux for 5 to 15 hours.

A compound of formula IV above wherein $R^4$ and $R^5$ have the meanings given can also be reacted with a compound of formula Va $$R^1R^2C=CHCO_2R^3$$

wherein $R^1$, $R^2$ and $R^3$ have the meanings given above, to the formation of a compound of formula I.

This reaction does not need a basic condensating agent or an excess of the compound Va.

Further, a compound of formula VI

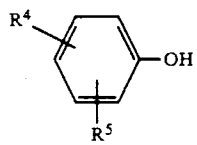

(VI)

wherein $R^4$ and $R^5$ have the same meanings as given above is reacted with a compound of formula VII

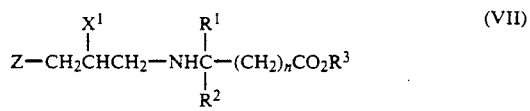

(VII)

wherein $R^1$, $R^2$, $R^3$, n, Z and $X^1$ have the same meanings as given above.

This reaction is carried out in a common way. In those cases where reactive esters are used as starting material, the compound of formula VI may suitably be used in the form of its metal phenolate as alkali metal phenolate, preferably sodiumphenolate, or one works in the presence of an acid binding agent, preferably a condensating agent, which can form a salt of the compound of formula VI as an alkali metal alcoholate.

This reaction is preferably carried out in an alkanol having 1 to 3 carbon atoms in an autoclave being heated to 80° to 100° C. for 1 to 15 hours.

Further, a compound of formula VI

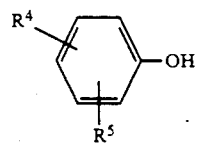

(VI)

wherein $R^4$ and $R^5$ have the same meanings as given above, is reacted with a compound of formula VIII

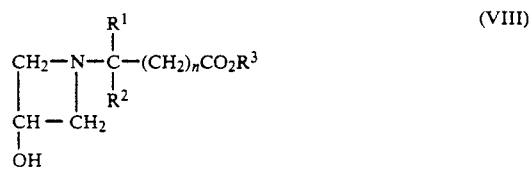

(VIII)

wherein $R^1$, $R^2$, $R^3$, and n have the meanings given above.

This reaction is carried out in a common way. Thus, the reaction is carried out under alkaline conditions in a suitable solvent, as benzylalcohol by boiling the reaction mixture for some hours. Thereby the phenol is primarily converted to its metal phenolate as alkali metal phenolate before it is added to the acetidinol of formula VIII.

Further, one may split off a residue from a compound of formula I above, in which the nitrogen atom of the amino group and/or the hydroxy groups have attached thereto a splitable residue.

Such splitable residues are especially those which are splitable by solvolysis, reduction, pyrolysis or fermentation.

At this splitting off of a residue the amino-substituent

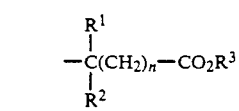

can be formed from another substituent $X^2$ containing one or more at these conditions so reacting functional groups. Such functional groups are carbon-carbon unsaturation. $R^4$ and/or $R^5$ can be formed simultaneously at this splitting off.

Residues splitable by solvolysis are preferably residues splitable by hydrolysis or ammonolysis.

Residues splitable by means of hydrolysis are e.g. an acyl residue, which, when present, also can be functionally varied carboxy groups, e.g. oxycarbonyl residues, as alkoxycarbonyl residues, e.g. tert.-butoxycarbonyl residue, or ethoxycarbonyl residue, aralkoxycarbonyl residues as phenylloweralkoxycarbonyl residues, e.g. a carbobenzyloxy residue halogencarbonyl residue, e.g. a chlorocarbon residue and carbamoyl groups. Further, arylsulphonyl residues as toluenesulfonyl or bromobenzenesulfonyl residues and possibly as halogenated, as fluorinated lower alkanoyl residues as formyl-, acetyl- or trifluoroacetyl residues or a benzyl residue or cyano groups or silyl residues, as trimethylsilyl residue.

Of the above mentioned residues present at the hydroxy groups, which residues are splitable by hydrolysis, preferably the oxycarbonyl residues and the loweralkanoyl residues or the benzoyl residues are used.

Besides the above mentioned also double-bound residues, which are splitable at the amino group by hydrolysis are used, e.g. alkylidene or benzylidene residue or a phosporylidene group as a triphenylphosphorylidene group, whereby the nitrogen atom then obtains a positive charge.

Residues splitable at the amino group by hydrolysis are furthermore divalent residues as in occurring cases substituted methylene. As substituents on the methylene residues any organic residue may be used, whereby it does not matter at the hydrolysis which compound is the substituent to the methylene residue. As methylene substituents e.g. aliphatic or aromatic residues as alkyl as mentioned above, aryl e.g. phenyl or pyridyl may be used. The hydrolysis may be carried out in any common way, suitably in a basic or preferably in an acid medium.

Compounds having residues being splitable by hydrolysis are also the compounds according to formula IX

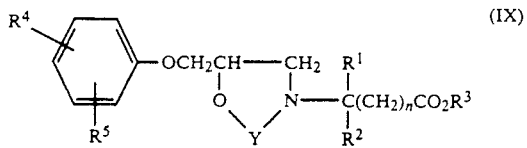

wherein $R^1$, $R^2$, $R^3$, $R^4$, $R^5$ and n have the same meanings as given above and Y is a carbonyl, thiocarbonyl, or a

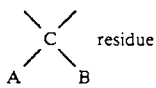

wherein A and B are each severally hydrogen, alkyl, alkylaryl or aryl.

The hydrolysis is carried out in an analogous way, e.g. in the presence of a hydrolysing agent, e.g. in the presence of an acidic agent as e.g. diluted mineral acids, as sulfuric acid or hydrohalogen acid, or in the presence of basic agents as e.g. alkalimetal hydroxides, as sodium hydroxide. Oxycarbonyl residues, aryl sulfonyl residues and cyano groups may in a suitable way be split off by means of acidic agents as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromo-cyano method" (v. Braun). Further, e.g. a tert.-butoxycarbonyl residue may be split off under anhydrous conditions by means of a treatment with a suitable acid, as trifluoracetic acid. Acidic agents are preferably used at a hydrolysis of compounds of formula IX.

Residues splitable by ammonolysis are especially the halogencarbonyl residues, as the chlorocarbonyl residue. The ammonolysis may be carried out in a common way, e.g. by means of an amine containing at least one hydrogen atom bound to the nitrogen atom, as a mono- or diloweralkylamine e.g. methylamine or dimethylamine, or especially ammonia, preferably at an elevated temperature. Instead of ammonia one may use an agent which gives ammonia as hexamethylenetetraamine.

Residues splitable by means of a reduction are e.g. an α-arylalkyl residue, as a benzyl residue or an α-aralkoxycarbonyl residue as a benzyloxycarbonyl residue, which in a common way may be split off by means of a hydrogenolysis, especially by catalytically activated hydrogen, as by hydrogen in the presence of hydrogenating catalysts, e.g. Raney-nickel. Further residues splitable by means of hydrogenolysis are 2-halogenalkoxycarbonyl residues as 2,2,2,-trichloroethoxycarbonyl residues or 2-iodoethoxy- or 2,2,2-tri-bromoethoxycarbonyl residues, which may be split off in a common way, suitably by means of a metallic reduction (so called nascerating hydrogen). Nascerating hydrogen may be obtained by the influence of metal or metal alloys, as amalgam on compounds which give hydrogen as carboxy acids, alcohols or water, whereby especially zinc or zinc alloys together with acetic acid may be used. Hydrogenolysis of 2-halogenalkoxycarbonyl residues may further take place using chromium or chromium (II) compounds as chromium (II) chloride or chromium (II) acetate.

A residue splitable by reduction may also be an arylsulfonyl group as a toluenesulfonyl group, which in a common way may be split off by reduction using nascerating hydrogen, e.g. by means of an alkali metal, as lithium or sodium in liquid ammonia, and suitably may be split off from a nitrogen atom. At the carrying out of the reduction one has to take care of the fact that other reducing groups are not influenced.

Residues splitable by means of pyrolysis, especially residues splitable from the nitrogen atom, are in occurring cases substituted suitably unsubstituted carbamoyl groups. Suitable substituents are e.g. loweralkyl or aryl-loweralkyl as methyl or benzyl or aryl, as phenyl, the pyrolysis is carried out in a common way, whereby one may have to take care of other thermically susceptible groups. Residues splitable by means of fermentation, especially residues splitable from the nitrogen atom are in occurring cases substituted, however, suitably unsubstituted carbamoyl groups. Suitable substituents are e.g. loweralkyl or aryl-loweralkyl, as methyl or benzyl, or aryl as phenyl. The fermentation is carried out in a common way, e.g. by means of the enzyme urease or soy bean extract at about 20° C. or slightly elevated temperature.

Further, a Schiff's base of formula X or XI

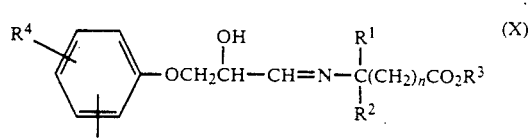

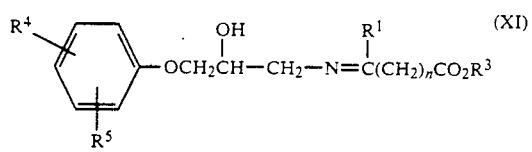

or a cyclic tautomer corresponding to formula XI or formula XII

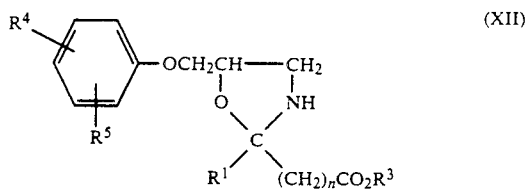

can be reduced, wherein $R^1$, $R^2$, $R^3$, $R^4$, $R^5$ and n have the same meanings as given above, and whereby the compounds of formula XI and XII may exist together, too.

This reduction is carried out in a common way, e.g. using a di-lightmetalhydride, as sodiumborohydride, lithiumaluminiumhydride, using a hydride as Boran with formic acid, or by means of a catalytic hydrogenation, as with hydrogen in the presence of Raney-nickel. At the reduction one has to take care of the fact that other groups are not affected.

Further, the oxo group in the compound of formula XIII

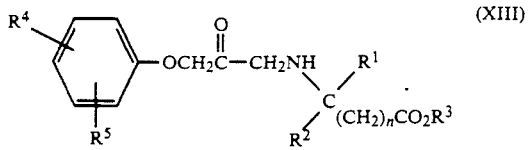

wherein $R^1$, $R^2$, $R^3$, $R^4$, $R^5$ and n have the same meanings as given above, can be reduced to a hydroxy group. This reduction is carried out in a common way, especially using a di-lightmetalhydride, as mentioned above, or according to the "Meerwein-Pondorf-Verley method" or a modification thereof, suitably using an alkanol as a reaction component and as solvent, as isopropanol, and using a metalalkanolate, as metalisopropanolate, e.g. aluminium isopropanolate.

Further, in a compound of formula XIV

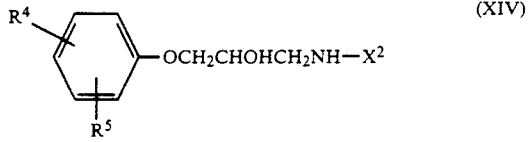

wherein $R^4$ and $R^5$ have the meanings given above, and $X^2$ is a residue, which is able to be transformed to a residue,

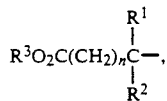

wherein $R^1$, $R^2$, $R^3$, and n have the meanings given above, one transforms $X^2$ to this residue.

$X^2$ can thus be a residue of the formula

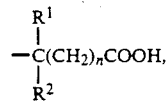

wherein $R^1$, $R^2$ and n have the meanings given above, which residue $X^2$ is esterified in accordance with processes known per se. Such processes are e.g. esterification in a common way using a strong acid as a catalyst and/or using any form of water removal.

The carboxylic acid can also be esterified by alkylation of the carboxylate in a common way using or not using ion pair technic.

Further the ester group can be formed at the esterification reaction from another functional group, e.g. from a nitril, reacting at these conditions.

The residue

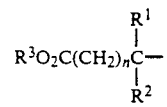

can also be obtained from $X^2$ by e.g. reduction of a carbon-carbon unsaturation and/or from another functional group as e.g. a keto group.

The residue

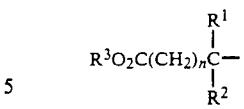

can also be obtained from $X^2$ by splitting off a functional group as a group containing a nitrogen atom, and the like. $R^1$, $R^2$, $R^3$, and n have the meanings given above.

The residue $X^2$ can also be of the formula

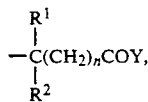

wherein Y is a leaving group, such as alkoxy, aryloxy, alkylcarboxy, halogen, etc. The transformation into

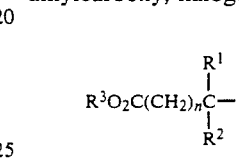

can then take place in different ways i.e. via methods as reesterification, esterification, and the like.

Thus, the following reactions can take place as examples of the above mentioned reactions, where $X^2$ is a group transformable into

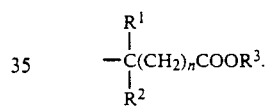

In the following $R^7$ is the group

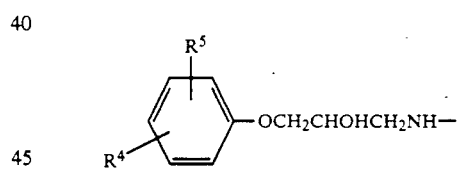

wherein $R^4$ and $R^5$ have the meanings given above:

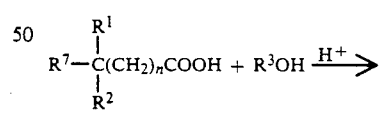

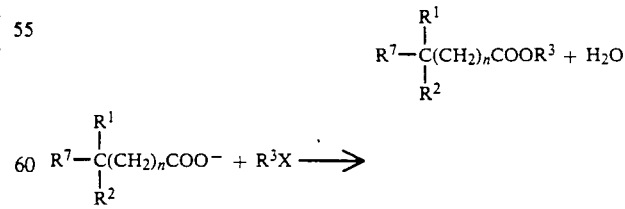

($X^-$ is e.g. $Cl^-$, $Br^-$, $I^-$)

-continued

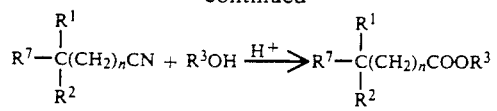

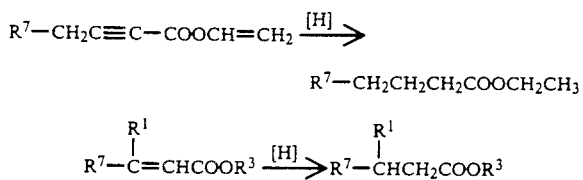

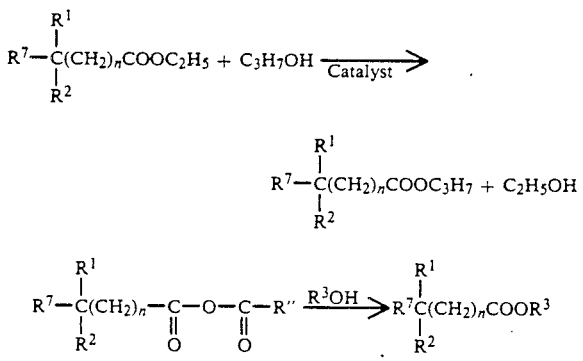

Further, the oxo group in a compound corresponding to these of formula I and which carries an oxo group at a carbon atom bound to a nitrogen atom may be reduced by two hydrogen atoms.

Said compounds are e.g. such of the formula XV

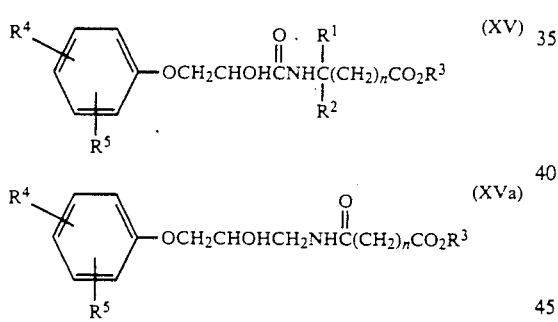

wherein $R^1$, $R^2$, $R^3$, $R^4$, $R^5$ and n have the meanings as given above.

The reduction can be carried out according to the above described manner using complex metalhydrides, e.g. borohydrides.

Further a compound of the present invention can be obtained by catalytic hydrogenation of a compound of the invention containing one or more substituents in the aromatic ring that can be split off by means of catalytic hydrogenation. Such substituents are F, Br, Cl and I. The splitting off can also take place in connection with prior mentioned methods.

Depending on the process conditions and the starting material the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using e.g. basic agents as alkali or ion exchanger. On the other hand, the free bases obtained may form salts with organic or inorganic acids. In the preparation of acid addition salts preferably such acids are used which form suitable therapeutically acceptable salts. Such acids are e.g. hydrohalogen acids, sulfuric acid, phosphoric acid, nitric acid, perchloric acid, aliphatic, aclicyclic, aromatic or heterocyclic, carboxy or sulfonic acids, as formic, acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicyclic or p-aminosalicyclic acid, embonic acid, methanesulfonic, ethanesulfonic, hydroxyethanesulfonic, ethylenesulfonic acids, halogenbenzenesulfonic, toluenesulfonic, naphtylsulphonic acids, or sulfanilic acid; methionine, tryptophane, lysine or arginine.

These or other salts of the new compounds as e.g. picrates may serve as purifying agents or the free bases obtained as the free bases are transformed into salts, these are separated and the bases are then set free from the salts again. According to the close relationship between the new compounds in free form and in the form of their salts it will be understood from the above and the below that, if possible, the corresponding salts are included in the free compound.

The invention also relates to any embodiment of the process of which one starts from any compound obtained as an intermediate in any process step and one carries out the lacking process step, or one breaks off the process at any step, or at which one forms a starting material under the reaction conditions, or at which a reaction component possibly in the form of its salt is present.

Thus, one may react an aldehyde of the formula XVI

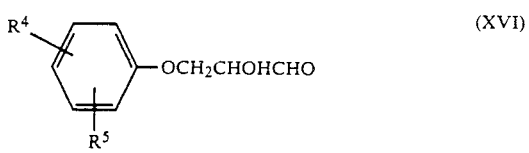

wherein $R^4$ and $R^5$ have the same meanings as given above, with an amine of the formula XVII

wherein $R^1$, $R^2$, $R^3$ and n have the meanings given above in the presence of a suitable reducing agent, as one of the above mentioned. Thereby a compound of formula X is obtained as an intermediate, which then is reduced according to the invention.

Further, one may in a manner known per se react an amine of the formula IV with a keton of the formula XVIII

wherein $R^1$, $R^3$ and n have the meanings given above, in the presence of a suitable reducing agent, as one of the above mentioned to produce compounds of formula XI or XII as an intermediate, which then is reduced according to the invention.

Further, in a compound of the formula XIX

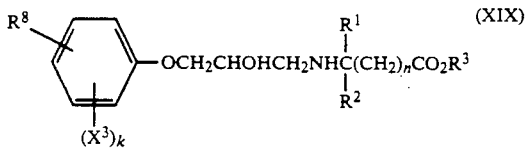

wherein $R^1$, $R^2$, $R^3$, and n have the same meanings as given above, and $R^8$ is either of $R^4$ and $R^5$ when k is 1, and $R^8$ is hydrogen when k is 2, and $X^3$ is a residue transformable into $R^4/R^5$, $X^3$ is transformed into $R^4/R^5$.

$X^3$ can thus be a carbon-carbon unsaturated residue and/or a carbonyl containing residue which residues are hydrogenated to give a residue $R^4/R^5$. Thus, an alkynyl or an alkynyloxy group can be hydrogenated to give an alkenyl group, or an alkenyloxy group, respectively, or an alkyl group, or an alkoxy group, respectively, depending on how far the hydrogenation is carried out.

Further, $X^3$ can be e.g. a residue

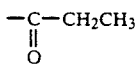

which is hydrogenated to give an alkyl $R^4/R^5$.

Further, $X^3$ can be a residue -OH, alkoxy-OH or alkyl-OH which is eterified in a known way to give an alkoxy, alkenyloxy, or alkynyloxy group $R^4/R^5$, or alkoxyalkyl, or alkoxyalkoxy, respectively.

Further, $X^3$ can be hydrogen, $R^4/R^5$ being halogen, preferably chloro and bromo can be added.

Thus, a compound of the formula

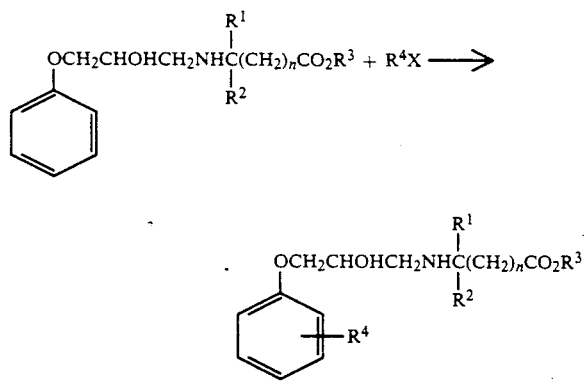

wherein $R^1$, $R^2$, $R^3$, $R^4$ and n have the meanings given above and X is halogen or $R^4X$ is, e.g., tert. butylhypochlorite.

The new compounds may, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may, depending on physical-chemical differences of the component, be separated into the both stereoisomeric (diastereomeric) pure racemate e.g. by means of chromatography and/or fractionated crystallization.

The racemates obtained can be separated according to known methods, e.g. by means of recrystallization from an optically active solvent, by means of microorganisms, or by a reaction with optically active acids forming salts of the compound and separating the salts thus obtained, e.g. by means of their different solubility in the diastereomers, from which the antipodes by the influence of a suitable agent may be set free. Suitably useable optically active acids are e.g. the L- and D- forms of tartaric acid, di-o-tolyltartaric acid, malic acid, mandelic acid, camphersulfonic acid or china acid. Preferably the more active part of the two antipodes is isolated. Further the two enantiomers can be obtained by asymmetrical reduction of the corresponding ketocompound.

Suitably such starting materials are used for carrying out the reactions of the invention, which material leads to groups of end products primarily especially desired and and especially to the specifically described and preferred end products.

The starting materials are known or may, if they should be new, be obtained according to processes known per se.

In clinical use the compounds of the invention are administered normally by injection in the form of a pharmaceutical preparation, which contains an active component either as free base or as pharmaceutically acceptable, non-toxic acid addition salts, e.g. the hydrochloride, lactate, acetate, sulphamate or the like in combination with a pharmaceutical carrier.

Thereby the mentioning of the new compounds of the invention is here related to either the free amine base or the acid addition salts of the free base, even if the compounds are generally or specifically described, provided that the context in which such expressions are used, e.g, in the examples, with this broad meaning should not correspond. The carrier may be a liquid diluent or a capsule. These pharmaceutical preparations are a further object of the invention. Usually the amount of active compound is between 0.1 to 99% by weight of the preparation, suitably between 0.5 to 20% by weight in preparations for injection.

Solutions for parenteral administration by injection may be prepared as an aqueous solution of a water soluble pharmaceutically acceptable salt of the active compound, preferably in a concentration from about 0.5% by weight to about 20% by weight. These solutions may also contain stabilizing agents and/or buffering agents and may suitably be available in different dosage unit ampoules.

The daily dose of the active substance varies and is depending on the acceptance but as a general rule it is 1-100 mg/minute of active substance at intravenous administration, (average weight human).

BEST MODE OF CARRYING OUT THE INVENTION

The following illustrates the principle and the adaption of the invention, however, without being limited thereto. Temperature is given in degrees Celsius.

EXAMPLE 1

Preparation of ethyl N-[3-(2-cyanophenoxy)-2-hydroxypropyl]-3-aminopropanoate (Method a)

15.36 g of the hydrochloride of ethyl 3-aminopropanoate and 6.2 g of potassium hydroxide were stirred in 150 ml of abs. ethanol until neutral reaction, ca 1 h. Under reflux was added 8.7 g of 2-(2,3-epoxypropoxy)benzonitrile in 125 ml of abs. ethanol. The mixture was refluxed for 8 h, filtered and evaporated. The residue was dissolved in ether, washed twice with water and extracted with 25 ml of 2-n hydrochloric acid. The aqueous phase was extracted with methylene chloride. The methylene chloride phase was dried over $Na_2SO_4$, filtered and evaporated to dryness. The hydrochloride of ethyl N-[3-(2-cyanophenoxy)-2-hydroxypropyl]-3-aminopropanoate crystallized. Yield 5.75 g. Melting point 120° C. (HCl). The structure was determined using NMR and equivalent weight.

EXAMPLE 2

Preparation of ethyl N-[3-(2-N-methylcarbamoylmethoxyphenoxy)-2-hydroxypropyl]-3-aminopropanoate This compound was prepared in accordance with Example 1 using 14.1 g of the hydrochloride of ethyl 3-aminopropanoate, 3.68 g of NaOH, and 12 g of 2-(2,3-epoxypropoxy)phenoxy-N-methylacetamide in isopropanol as a solvent. The crude oil was dissolved in $CH_2Cl_2$, washed three times with water, dried over $Na_2SO_4$, and evaporated. The residue was dissolved in 200 ml of ethyl acetate and 200 ml of water was added. The pH was adjusted to 5.0 with 2-n HCl. The water phase was separated and adjusted to pH 9.0 with 2-n NaOH and extracted with ethyl acetate, dried over $Na_2SO_4$, filtered and evaporated. The oily residue was crystallized by treating with diisopropyl ether/diethyl ether 4/1. The crystals were washed with diethyl ether. Yield 1.3 g. Melting point 80° C. (base). The structure was determined using NMR and equivalent weight.

EXAMPLE 3

Preparation of ethyl N-[3-(3-cyanophenoxy)-2-hydroxypropyl]-3-aminopropanoate

This compound was prepared in accordance with Example 1 using 15.36 g of the hydrochloride of ethyl 3-aminopropanoate, 8.7 g of 3-(2,3-epoxypropoxy)benzonitrile, and 4.0 g of NaOH. The crude oil was dissolved in 200 ml of ethyl acetate, washed twice with water, and extracted with 2-n HCl. The pH of the water phase was adjusted to 9.5 and the solution extracted with ethyl acetate. The ethyl acetate phase was dried with $MgSO_4$, filtered and evaporated. Ethyl N-[3-(3-cyanophenoxy)-2-hydroxypropyl]-3-aminopropanoate crystallized. Yield 2 g. Melting point 95° C. (base). The structure was determined using NMR.

EXAMPLE 4

Preparation of ethyl N-[3-[4-(2-N'-isopropylureido)ethylphenoxy]-2-hydroxypropyl]-3-aminopropanoate This compound was prepared in accordance with Example 1 using 14.0 g of the hydrochloride of ethyl 3-aminopropanoate, 11.2 g of N-[2-[4-(2,3-epoxypropoxy)phenyl]ethyl]-N'-isopropylurea, and 3.2 g of NaOH. The crude crystals were washed with $H_2O$ and dissolved in a mixture of 500 ml $H_2O$ and 25 ml 2-n HCl. (The undissolved crystals were filtered off). The base of ethyl N-[3-[4-(2-N'-isopropylureido)-ethylphenoxy]-2-hydroxylpropyl]-3-aminopropanoate was crystallized by treating the water phase with 25 ml of 2-n NaOH. The hydrochloride of ethyl N-[3-[4-(2-N'-isopropylureido)ethylphenoxy]-2-hydroxylpropyl]-3-aminopropanoate was prepared by dissolving in acetone and adding an equivalent amount of hydrochloric acid. Yield 2.8 g. Melting point 185° C. (HCl). The structure was determined by NMR.

EXAMPLE 5

Preparation of ethyl N-[3-(3-methylphenoxy)-2-hydroxypropyl]-3-aminopropanoate

This compound was prepared in accordance with Example 1 using 15.36 g of the hydrochloride of ethyl 3-aminopropanoate, 8.2 g of 1,2-epoxy-3-o-tolyloxypropane, and 4.0 g NaOH. The crude product was treated with 200 ml of water and the pH was adjusted to 3.0 with 2-n HCl. The solution was decanted and washed with ethyl acetate. The water phase was treated with $NaHCO_3$ and the product was extracted with ethyl acetate. The ethyl acetate phase was dried over $MgSO_4$, filtered, and evaporated. The product was recrystallized from diisopropyl ether. Yield 3.0 g. Melting point 57° C. (base). The structure was determined using NMR.

EXAMPLE 6

Preparation of ethyl N-[3-(2-allyl-4-carbamoylmethylphenoxy)-2-hydroxypropyl]-3-aminopropanoate This compound was prepared in accordance with Example 1 using 10.8 g of the hydrochloride of ethyl 3-aminopropanoate, 11.6 g of 3-allyl-4-(2,3-epoxypropoxy)phenylacetamide, and 2.84 g NaOH. The crude product was crystallized from ethyl acetate. Yield 1.7 g. Melting point 98° C. (base). The structure was determined using NMR and equivalent weight.

EXAMPLE 7

Preparation of ethyl N-[3-(2-cyano-4-methoxyphenoxy)-2-hydroxypropyl]-3-aminopropanoate This compound was prepared in accordance with Example 1 using 6.9 g of the hydrochloride of ethyl 3-aminopropanoate, 6.0 g of 5-methoxy-2-(2,3-epoxypropoxy)benzonitrile, and 1.8 g of NaOH. The crude oil was treated with ether and ethyl N-[3-(2-cyano-4-methoxyphenoxy)-2-hydroxypropyl]-3-aminopropanoate crystallized. Yield 0.9 g. Melting point 76° C. (base). The structure was determined using NMR and equivalent weight.

EXAMPLE 8

Preparation of ethyl N-[3-(3-methoxyphenoxy)-2-hydroxypropyl]-3-aminopropanoate

This compound was prepared in accordance with Example 1 using 7.6 g of the hydrochloride of ethyl 3-aminopropanoate, 4.5 g of 3-(3-methoxyphenoxy)-1,2-epoxypropane, and 2.0 g of NaOH. The crude product was washed with 150 ml of water and dissolved in 100 ml of water and 10 ml of 2-n HCl. This solution was extracted with ethyl acetate, treated with NaHCO$_3$, and extracted with CH$_2$Cl$_2$. The organic layer was separated, dried over MgSO$_4$, filtered and evaporated. Ethyl N-[3-(2-cyano-4-methoxyphenoxy)-2-hydroxypropyl]-3-aminopropanoate crystallized. Yield 1.2 g. Melting point 72° C. (base). The structure was determined by NMR.

EXAMPLE 9

Preparation of ethyl N-[3-(2,3-dimethylphenoxy)-2-hydroxypropyl]-3-aminopropanoate This compound was prepared in accordance with Example 8 using 7.6 g of the hydrochloride of ethyl 3-aminopropanoate, 4.5 g of 3-(2,3-dimethylphenoxy)-1,2-epoxypropane, and 2.0 g of NaOH. The hydrochloride of ethyl N-[3-(2,3-dimethylphenoxy)-2-hydroxypropyl]-3-aminopropanoate was prepared by dissolving the base in ethyl acetate and introducing an equivalent amount of hydrogen chloride gas. Yield 2.6 g. Melting point 121° C. (HCl). The structure was determined using NMR analysis.

EXAMPLE 10 (METHOD D)

9.0 g of 2-(2,3-epoxypropoxy)benzonitrile in 100 ml of ethanol was saturated with gaseous ammonia and the mixture was heated in an autoclave on a waterbath for 1 hour. The solvent was evaporated and the residue was dissolved in ethyl acetate and HCl-gas was introduced. The hydrochloride then precipitated, was filtered off and dissolved in 100 ml of ethanol to which 7.0 g of K$_2$CO$_3$ and 10.0 g of ethyl propenoate had been added. The mixture was refluxed for 2 hours and filtered whereupon the solvent was evaporated. The residue was dissolved in ethyl acetate. The hydrochloride of ethyl N-[3-(2-cyanophenoxy)-2-hydroxypropyl]-3-aminopropanoate was precipitated by introducing an equivalent amount of hydrogen chloride gas. Melting point 120° C.

EXAMPLE 11 (METHOD C)

1.2 g of Na were dissolved in 50 ml of ethanol, whereupon 5.95 g of 2-hydroxybenzonitrile and 10.4 g of ethyl N-(3-chloro-2-hydroxypropyl)-3-aminopropanoate were added. The mixture was heated under reflux for 6 hours. Thereupon it was filtered and the filtrate was evaporated to dryness. The residue was made acid to pH 3 using dilute HCl and extracted first with ether and thereafter with methylene chloride. The methylene chloride phase was dried over MgSO$_4$ and filtered. After evaporation of the solvent the hydrochloride of ethyl N-[3-(2-cyanophenoxy)-2-hydroxypropyl]-3-aminopropanoate crystallized. Melting point 120° C.

EXAMPLE 12 (METHOD D)

0.12 moles of 2-hydroxybenzonitrile were mixed with 0.080 moles of ethyl 3-(3-hydroxyazacyclobutyl)-propanoate, 0.500 moles of benzylalcohol and 0.002 moles of KOH. The mixture was refluxed while stirring for 6 hours at 140° C. and was then cooled and extracted with 1N HCl. The aqueous phase was extracted with ether and thereafter with methylene chloride. The methylene chloride phase was dried with MgSO$_4$, filtered and evaporated. The hydrochloride of ethyl N-[3-(2-cyanophenoxy)-2-hydroxypropyl]-3-aminopropanoate thus obtained melted at 120° C.

EXAMPLE 13 (METHOD F)

In accordance with Example 10 above 2-(3-amino-2-hydroxypropoxy)benzonitrile was prepared. 1.9 g of this compound were dissolved in 30 ml of methanol and 1.16 g of ethyl 3-oxopropanoate were added, wereby ethyl N-[3-(2-cyanophenoxy)-2-hydroxypropyl]-3-iminopropanoate was obtained. The solution was cooled to 0° C. and at this temperature 3 g of sodium borohydride were added little by little, whereby the imino compound was reduced. The temperature was then allowed to rise to ambient temperature and after 1 hour 100 ml of H$_2$O were added and the total mixture was extracted with ethyl acetate. The ethyl acetate phase was dried over MgSO$_4$ and filtered. The residue was transformed into its hydrochloride. In this way ethyl N-[3-(2-cyanophenoxy)-2-hydroxypropyl]-3-aminopropanoate hydrochloride was obtained. Melting point 120° C.

EXAMPLE 14 (METHOD G)

1 g of ethyl N-[3-(2-cyanophenoxy)-2-oxopropyl]-3-aminopropanoate was dissolved in 30 ml of methanol and the solution was cooled to 0° C. on an ice-bath. 1.0 g of NaBH$_4$ was added little by little while stirring first at 0° C. for 1 hour and then at ambient temperature for 0.5 hour. The solution thus obtained was evaporated whereupon 50 ml of H$_2$O were added. The aqueous phase was extracted with ethyl acetate. The organic phase was dried over MgSO$_4$ and filtered. The hydrochloride of ethyl N-[3-(2-cyanophenoxy)-2-hydroxypropyl]-3-aminopropanoate was precipitated by introducing an equivalent amount of hydrogen chloride gas. Melting point 120° C.

EXAMPLE 15 (METHOD C+H)

2.0 g of vinyl N-benzyl-N-[3-(2-cyanophenoxy)-2-hydroxypropyl]-3-aminopropanoate hydrochloride were dissolved in 100 ml of ethanol. 0.3 g of Pd/C (5%)-catalyst were added and the mixture was hydrogenated until 230 ml of hydrogen had been absorbed. The catalyst was filtered off and the solvent was evaporated. The hydrochloride of ethyl N-[3-(2-cyanophenoxy)-2-hydroxypropyl]-3-aminopropanoate melted at 120° C.

EXAMPLE 16 (METHOD H)

2.0 g of N-[3-(2-cyanophenoxy)-2-hydroxypropyl]-3-aminopropanoic acid were dissolved in 100 ml of ethanol. The solution was saturated with gaseous HCl and refluxed for 6 hours. The excess of ethanol was evaporated in vacuo and the residue crystallized. The hydrochloride of ethyl N-[3-(2-cyanophenoxy)-2-hydroxypropyl]-3-aminopropanoate melted at 120° C.

EXAMPLE 17 (METHOD H)

2.0 g of methyl N-[3-(2-cyanophenoxy)-2-hydroxypropyl]-3-aminopropanoate were dissolved in 100 mls of ethanol. The solution was treated with gaseous HCl and refluxed over night. After evaporation of excess of alkanols the hydrochloride of ethyl N-[3-(2-cyanophenoxy)-2-hydroxypropyl]-3-aminopropanoate was obtained. Melting point 120° C.

EXAMPLE 18

Preparation of propyl N-[3-(2-cyanophenoxy)-2-hydroxypropyl]-3-aminopropanoate

This compound was prepared in accordance with Example 1 using 6.8 g of the hydrochloride of propyl 3-aminopropanoate, 5.5 g of 2-(2,3-epoxypropoxy)benzonitrile, and 1.8 g of NaOH. The crude oil was treated with ether and propyl N-[3-(2-cyanophenoxy)-2-hydroxypropyl]-3-aminopropanoate crystallized. Yield 1.5 g. Melting point 89° C. (HCl). The structure was determined using NMR and equivalent weight.

EXAMPLE 19

Preparation of pentyl N-[3-(2-cyanophenoxy)-2-hydroxypropyl]-3-aminopropanoate

This compound was prepared in accordance with Example 1 using 6.9 g of the hydrochloride of pentyl 3-aminopropanoate, 5.5 g of 2-(2,3-epoxypropoxy)benzonitrile and 1.8 g of NaOH. The crude oil was treated with ether and butyl N-[3-(2-cyanophenoxy)-2-hydroxypropyl]-3-aminopropanoate crystallized. Yield 1.3 g. Melting point 91° C. (HCl). The structure was determined using NMR and equivalent weight.

EXAMPLE 20

3-[2-(4-hydroxyphenoxy)ethylamino]-3-o-methylphenoxypropanol-2 hydrochloride (1 g), sodiumchloride (0.8 g) and ascorbic acid (0.1 g) were dissolved in sufficient amount of distilled water to give 100 ml of solution. This solution, which contains 10 mg of active substance per each ml, was used in filling ampoules, which were sterilized.

BIOLOGICAL EFFECTS

The beta-adrenocaptor blocking agents of the present invention were tested as regards their biological properties. All compounds were thereby tested in two different experimental models but with the same species, premedication and preparation. Cats (males and females weighing 2.5-3.5 kg) were pretreated with reserpine (5 mg/kg bodyweight administered intraperitoneally) about 16 hours before the experiments.

The animals were pretreated with reserpine in order to eliminate the endogenous sympathetic control of heart rate and vescular smooth muscle tone. The cats were anaesthetized with pentobarbital (30 mg/kg bodyweight administered i.p.) and artificially ventilated with room air. A bilateral vagotomy was performed in the neck. Blood pressure was obtained from a cannulated carotid artery and heart rate was recorded from a cardiotachometer, triggered by the oscillations in blood pressure. The femoral artery of one hind leg was cannulated in both directions. Blood taken from the proximal part was pumped, at a constant flow-rate, back into the distal part of the artery by means of a roller pump (Watson-Marlow). The perfusion pressure (PP) was recorded. Changes in PP indicated changes in the peripheral vascular resistance of the leg.

EXPERIMENT A

The maximal heart rate and vasodilator responses to isoprenaline were established by injecting a high i.v. bolus dose of isoprenaline (2.0 μmol/kg). An isoprenaline infusion rate was then established which gave a heart rate response (at steady state) which was about 80% of the maximal heart rate response to isoprenaline. Usually this dose of isoprenaline was 0.25 μmol/kg×min. The vasodilator response to this dose of isoprenaline was also approximately 80% of maximal. The isoprenaline dose was then infused during periods of 20 minutes with an interval of 20 minutes between the infusion periods.

The test compound was administered as an intravenous bolus injection seven minutes after start of each isoprenaline infusion. The dose of the test compound was increased until total blockade of the isoprenaline responses was achieved.

For each dose of the test compound the peak reduction of the isoprenaline heart rate response was expressed as per cent blockade according to the formula:

$$100 \times \frac{\text{Reduction of the isoprenaline induced heart rate response (beats/min)}}{\text{Control isoprenaline response (beats/min)}}$$

Per cent blockade (for each dose) was then plotted against log dose of the test compound. The ED:50 value (i.e. the dose which produced half maximal blockade) was interpolated.

The plasma half life was estimated by the method of Levy (Nagashima, R., O'Reilly, R. A. and Levy, G., Clin. Pharmacol. Ther., 10 (1969) 22). The time from the peak inhibitory effect of each dose until 50% recovery was determined and plotted against log dose of the compound. The slope of the line obtained was calculated with linear regression. The slope equals $2.303/K_E$ where $K_E$ is the rate constant for elimination. The plasma half life (t ½) was then calculated according to the relation $t\frac{1}{2} = 0.693/K_E$.

EXPERIMENT B

The maximal heart rate and vasodilator responses to isoprenaline were established by injecting a high i.v. bolus dose of isoprenaline (2.0 μmol/kg). An isoprenaline bolus dose which gave a heart rate response which was about 80% of the maximal response was then tested out. Usually this dose of isoprenaline was 0.4 μmol/kg. The vasodilator response to this dose of isoprenaline was also approximately 80% of maximal.

The test compound was then infused intravenously in increasing doses. Each dose was given during 12 minutes with an interval of 18 minutes between doses.

The control dose of ispranaline was injected 10 minutes after start of each infusion of the test compound. The dose of the test compound was increased logarithmically until total blockade of the isoprenaline responses was achieved.

The inhibitory effect of each dose of the test compound was expressed as per cent blockade according to the formula:

$$100 \times \frac{\text{predrug isoprenaline response} - \text{isoprenaline response during test compound infusion}}{\text{predrug isoprenaline response}}$$

Per cent blockade was then plotted against log dose of the blocker and the ED:50-value was interpolated (of. above). The ED:50 for heart rate blockade and ED:50 for blockade of the vasodilatation could then be compared and the selectivity for the compound estimated. Intrinsic sympathomimetic activity was evaluated as the maximal heart rate elevation during infusion of the test compound.

The experiments demonstrate that the compounds of the invention are potent beta-adrenoceptor antagonists with a higher potency as regards blockade of the cardiac betaadrenoceptors than of vascular beta-adrenoceptors. Furthermore, the estimated plasma half lifes of the compounds are shorter than ten minutes.

|  | Experiment A | | | Experiment B | | |
|---|---|---|---|---|---|---|
|  | Blockade of isoprenaline induced effects | | | Blockade of isoprenaline induced effects | | Intrinsic |
| Compound acc. to | Heart rate ED:50 μmol/kg | Vasodilatation ED:50 μmol/kg | Calculated plasma half life t ½ min | Heart rate ED:50 μmol/kg × min | Vasodilatation ED:50 μmol/kg × min | sympathomimetic activity ISA beats/min (%) |
| Ex. 1 | 1.4 | 0.5 | 2.8 | 0.13 | 1.7 | +7 (9) |
| Ex. 2 | 0.1 | 0.15 | 7.2 | 0.16 | 0.8 | ±0 |
| Ex. 3 | 0.47 | 1.3 | — | 0.17 | 14.0 | +32 (36) |
| Ex. 4 | — | — | — | 0.44 | >6.4 | ±0 |
| Ex. 5 | 1.2 | 1.1 | 2.9 | 0.7 | 1.4 | ±0 |
| Ex. 6 | 0.08 | 1.2 | 6.0 | 0.32 | 1.1 | ±0 |
| Ex. 7 | 6.0 | — | 2.2 | 1.9 | >6.4 | ±0 |
| Ex. 8 | 2.3 | 0.48 | 2.7 | x | x | x |
| Ex. 9 | 5.3 | 3.5 | — | x | x | x |
| Ex. 18 | x | x | x | x | x | x |
| Ex. 19 | x | x | x | x | x | x | x = not investigated
— = not possible to calculate

We claim:

1. A compound of the formula I

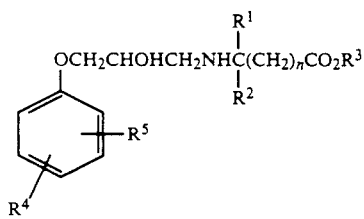

wherein $R^1$ and $R^2$ are each severally hydrogen, $R^3$ is alkyl having up to 7 carbon atoms, $R^4$ is selected from the group consisting of hydrogen, lower alkyl having up to 4 carbon atoms, lower alkenyl having up to 4 carbon atoms, lower alkoxy having up to 4 carbon atoms, cyano, $-(O)_n(CH_2)_mCONHR^6$, wherein $R^6$ is hydrogen or lower alkyl having up to 7 carbon atoms, n is an integer 0 or 1, and m is an interger 0, 1, 2 or 3, or $-(CH_2)_mNHCONHR^6$, wherein $R_6$ and m have the meanings given above, $R^5$ is $-(CH_2)_mNHCONHR^6$, wherein $R^6$ and m have the meanings given above, or a therapeutically acceptable salt of such a compound.

2. A pharmaceutical preparation intended for continuous intravenous administration for the treatment of acute myocardial infarction in a mammal, which preparation comprises at least one β-receptor blocking phenoxy-hydroxypropylamine compound according to claim 1, in association with a liquid pharmaceutically acceptable carrier, said compound being presented in an amount effective to provide β-receptor blocking activity in said mammal.

3. The method of treating acute myocardial infarction comprising administering to a mammal suffering from such infarction a therapeutically effective amount of a compound of claim 1 by way of continuous intravenous administration.

4. The method according to claim 3, wherein the compound is administered in an amount of 0.5–1.5 μmoles per kg body weight and minute.

5. Ethyl N-3-aminopropanoate, or a therapeutically acceptable salt thereof.

* * * * *